(12) United States Patent
Green et al.

(10) Patent No.: US 11,234,812 B2
(45) Date of Patent: Feb. 1, 2022

(54) METHODS FOR SURGICAL VALVE EXPANSION

(71) Applicant: St. Jude Medical, Cardiology Division, Inc., St. Paul, MN (US)

(72) Inventors: Chad Joshua Green, Forest Lake, MN (US); Neelakantan Saikrishnan, Plymouth, MN (US); Paul E. Ashworth, Danbury, WI (US); Scott R. Lien, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 343 days.

(21) Appl. No.: 16/388,185

(22) Filed: Apr. 18, 2019

(65) Prior Publication Data

US 2019/0321170 A1    Oct. 24, 2019

Related U.S. Application Data

(60) Provisional application No. 62/659,423, filed on Apr. 18, 2018.

(51) Int. Cl.
*A61F 2/24* (2006.01)

(52) U.S. Cl.
CPC .......... *A61F 2/2418* (2013.01); *A61F 2/2409* (2013.01); *A61F 2/2433* (2013.01); *A61F 2/2442* (2013.01); *A61F 2250/006* (2013.01)

(58) Field of Classification Search
CPC .... A61F 2/2418; A61F 2250/001; A61F 2/24; A61F 2250/006; A61F 2250/0071
USPC ...................................................... 623/2.17
See application file for complete search history.

(56) References Cited

U.S. PATENT DOCUMENTS

| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |

(Continued)

FOREIGN PATENT DOCUMENTS

| AU | 2002212418 B2 | 3/2006 |
| DE | 19857887 B4 | 5/2005 |

(Continued)

OTHER PUBLICATIONS

Allen, K.B. et al., "Bioprosthetic Valve Fracture to Facilitate Transcatheter Valve-in-Valve Implantation", Ann Thorac Surg., Jun. 29, 2017, pp. 1501-1508.

(Continued)

*Primary Examiner* — Brian E Pellegrino
(74) *Attorney, Agent, or Firm* — Lerner, David, Littenberg, Krumholz & Mentlik, LLP

(57) ABSTRACT

A surgical heart valve includes a non-collapsible frame having features that enable the frame to expand from an initial condition having a first diameter to an expanded condition having a second diameter larger than the first diameter after the valve has been implanted within a patient. The frame may include members that prevent the unintended expansion of the frame, such as during implantation, and members that prevent the over-expansion of the frame. The surgical heart valve further includes a valve assembly connected to the frame and including a plurality of leaflets.

7 Claims, 6 Drawing Sheets

(56) References Cited

U.S. PATENT DOCUMENTS

| | | |
|---|---|---|
| 4,994,077 A | 2/1991 | Dobben |
| 5,411,552 A | 5/1995 | Andersen et al. |
| 5,480,423 A | 1/1996 | Ravenscroft et al. |
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,258,117 B1* | 7/2001 | Camrud .............. A61F 2/90 623/1.16 |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 8,613,765 B2 | 12/2013 | Bonhoeffer et al. |
| 8,840,661 B2 | 9/2014 | Manasse |
| 9,504,556 B2 | 11/2016 | Bebb et al. |
| 9,510,944 B2 | 12/2016 | Cai et al. |
| 10,080,653 B2 | 9/2018 | Conklin et al. |
| 2001/0020181 A1 | 9/2001 | Layne |
| 2002/0036220 A1 | 3/2002 | Gabbay |
| 2003/0023303 A1 | 1/2003 | Palmaz et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2005/0096726 A1 | 5/2005 | Sequin et al. |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2012/0303116 A1 | 11/2012 | Gorman, III et al. |
| 2014/0188221 A1 | 7/2014 | Chung et al. |
| 2016/0045312 A1* | 2/2016 | Braido ............ A61F 2/2445 623/2.37 |
| 2016/0074165 A1 | 3/2016 | Spence et al. |

FOREIGN PATENT DOCUMENTS

| | | |
|---|---|---|
| DE | 10121210 B4 | 11/2005 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1621162 A2 | 2/2006 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 01056500 A2 | 8/2001 |
| WO | 2001054625 A1 | 8/2001 |
| WO | 2001076510 A2 | 10/2001 |
| WO | 2002036048 A1 | 5/2002 |
| WO | 0247575 A2 | 6/2002 |
| WO | 2003047468 A1 | 6/2003 |
| WO | 2005070343 A1 | 8/2005 |
| WO | 06073626 A2 | 7/2006 |
| WO | 2009108355 A1 | 9/2009 |

(56) References Cited

FOREIGN PATENT DOCUMENTS

| WO | 10008548 A2 | 1/2010 | |
|---|---|---|---|
| WO | 2010008549 A1 | 1/2010 | |
| WO | 2010096176 A1 | 8/2010 | |
| WO | 2010098857 A1 | 9/2010 | |
| WO | 2012018779 A2 | 2/2012 | |
| WO | WO-2013114214 A2 * | 8/2013 | ........... A61F 2/2427 |
| WO | 2014105741 A1 | 7/2014 | |

OTHER PUBLICATIONS

Andersen, et al., "Transluminal Implantation of Artificial Heart Valves. Description of a New Expandable Aortic Valve and Initial Results with Implantation by Catheter Technique in Closed Chest Pigs", European Heart Journal, vol. 13, No. 5, May 1992, pp. 704-708.

Andersen, H.R., "Transluminal Catheter Implanted Prosthetic Heart Valves", International Journal of Angiology, vol. 7, No. 02, Mar. 1998, pp. 102-106.

Braido, et al., "Surgical Stent Assembly", Design U.S. Appl. No. 29/375,243, filed Sep. 20, 2010.

Dewey, et al., "Transapical Aortic Valve Implantation: An Animal Feasibility Study", The Annals of Thoracic Surgery, vol. 82, No. 1, Jul. 2006, pp. 110-116.

Hijazi, et al., "Transcatheter Valve Repair", CRC Press, Jan. 2006, 31 pages.

Huber, et al., "Direct-Access Valve Replacement: A Novel Approach for Off-Pump Valve Implantation Using Valve Stents", Journal of the American College of Cardiology, vol. 46, No. 2, Jul. 2005, pp. 366-370.

Knudsen, et al., "Catheter-Implanted Prosthetic Heart Valves: Transluminal Catheter Implantation of a New Expandable Artificial Heart Valve in the Descending Thoracic Aorta in Isolated Vessels and Closed Chest Pigs", The International Journal of Artificial Organs, vol. 16, No. 5, May 1993, pp. 253-262.

Lichtenstein, et al., "Transapical Transcatheter Aortic Valve Implantation in Humans: Initial Clinical Experience", Circulation, vol. 114, Jul. 2006, pp. 591-596.

Lightenstein, S.V., "Closed Heart Surgery: Back to the Future", The Journal of Thoracic and Cardiovascular Surgery, vol. 131, No. 5, pp. 941-943.

Mack, M.J., "Minimally Invasive Cardiac Surgery", Surgical Endoscopy and Other Interventional Techniques, vol. 20, No. 2, Apr. 2006, pp. S488-S492.

Moazami, et al., "Transluminal Aortic Valve Placement: A Feasibility Study with a Newly Designed Collapsible Aortic Valve", ASAIO Journal (American Society for Artificial Internal Organs, vol. 42, No. 5, 1992, pp M381-M385.

Walther, et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb, et al., "Percutaneous Aortic Valve Implantation Retrograde from the Femoral Artery", Circulation, vol. 113, No. 6, Feb. 2006, pp. 842-850.

Zegdi, et al., "Is It Reasonable to Treat All Calcified Stenotic Aortic Valves with a Valved Stent?: Results From a Human Anatomic Study in Adults", Journal of the American College of Cardiology, vol. 51, No. 5, Feb. 2008, pp. 579-584.

Extended European Search Report including Written Opinion for Application No. EP19170020.2, dated Aug. 21, 2019, pp. 1-8.

* cited by examiner

METHODS FOR SURGICAL VALVE EXPANSION

CROSS-REFERENCE TO RELATED APPLICATIONS

The present application claims the benefit of the filing date of U.S. Provisional Patent Application No. 62/659,423 filed on Apr. 18, 2018, the disclosure of which is hereby incorporated herein by reference.

BACKGROUND OF THE INVENTION

The present disclosure relates in general to a heart valve for heart valve replacement and, in particular, to bioprosthetic heart valves. More particularly, the present disclosure relates to surgical heart valves that facilitate the performance of subsequent valve-in-valve implantation procedures.

When a native heart valve in an individual is diseased or damaged, a bioprosthetic heart valve may be surgically implanted in that individual to replace the native heart valve. At some time after the bioprosthetic heart valve has been successfully implanted within the individual, the heart valve may become damaged or worn out such that it ceases to function properly. If the implanted heart valve fails to function properly, a new replacement prosthetic heart valve may be surgically implanted to resume normal functions. However, at the point at which the original implanted heart valve needs replacement, patients are often too old and frail for another invasive surgical procedure. For these patients, a less traumatic valve-in-valve procedure (hereinafter referred to as "VIV procedure") may be performed. In a VIV procedure, a new prosthetic heart valve is implanted inside of the surgical heart valve using a minimally invasive transcatheter procedure.

One challenge that arises from VIV procedures is that the diameter of the surgical heart valve limits the size of the transcatheter heart valve that can be implanted inside of it. When the originally implanted surgical valve is small (e.g., 19 or 21 millimeters in diameter), the size of the implanted transcatheter heart valve may be too small to the meet the patient's blood flow requirements. This results in the phenomenon of patient-prosthesis mismatch (hereinafter referred to as "PPM"). PPM has shown to be associated with increased mortality after VIV procedures. Thus, there exists a need for a mechanism by which surgical heart valves can be expanded in vivo so that they can accept a sufficiently-sized transcatheter valve and minimize the potential for PPM.

BRIEF SUMMARY OF THE INVENTION

According to a first embodiment of the present disclosure, a prosthetic heart valve includes a non-collapsible annular frame having annularly spaced commissure posts and an annulus portion disposed adjacent an inflow edge. The frame is configured to expand from an initial condition having a first diameter to an expanded condition having a second diameter larger than the first diameter when a predetermined force is applied to an inner surface of the frame. A valve assembly is connected to the frame and includes a plurality of leaflets.

According to another embodiment of the present disclosure, a prosthetic heart valve includes an annular base formed of a coil having a plurality of turns. The base is configured to expand from an initial condition having a first diameter to an expanded condition having a second diameter larger than the first diameter when a predetermined force is applied to an inner surface of the base. The prosthetic heart valve includes a leaflet frame having a plurality of annularly spaced commissure posts and a valve assembly connected to the frame at the commissure posts. The valve assembly includes a plurality of leaflets.

According to yet another embodiment of the present disclosure, a method of implanting a transcatheter heart valve within a surgical heart valve previously implanted in a patient includes expanding a diameter of the previously implanted surgical heart valve from a first diameter to a second diameter larger than the first diameter; and deploying a transcatheter heart valve within the previously implanted surgical heart valve.

In another embodiment, a system for repairing a damaged native heart valve includes a surgical heart valve having a non-collapsible annular frame with annularly spaced commissure posts and an annulus portion disposed adjacent an inflow edge. A valve assembly is connected to the frame and includes a plurality of leaflets. The frame is configured to expand from an initial condition having a first diameter to an expanded condition having a second diameter larger than the first diameter when a predetermined force is applied to an inner surface of the frame. The system includes a transcatheter heart valve deployable within the surgical heart valve and configured to properly function when the frame of the surgical heart valve is in the expanded condition

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the circumferential direction refers to a direction extending along the circumference of the prosthetic heart valve.

Figure 1A:
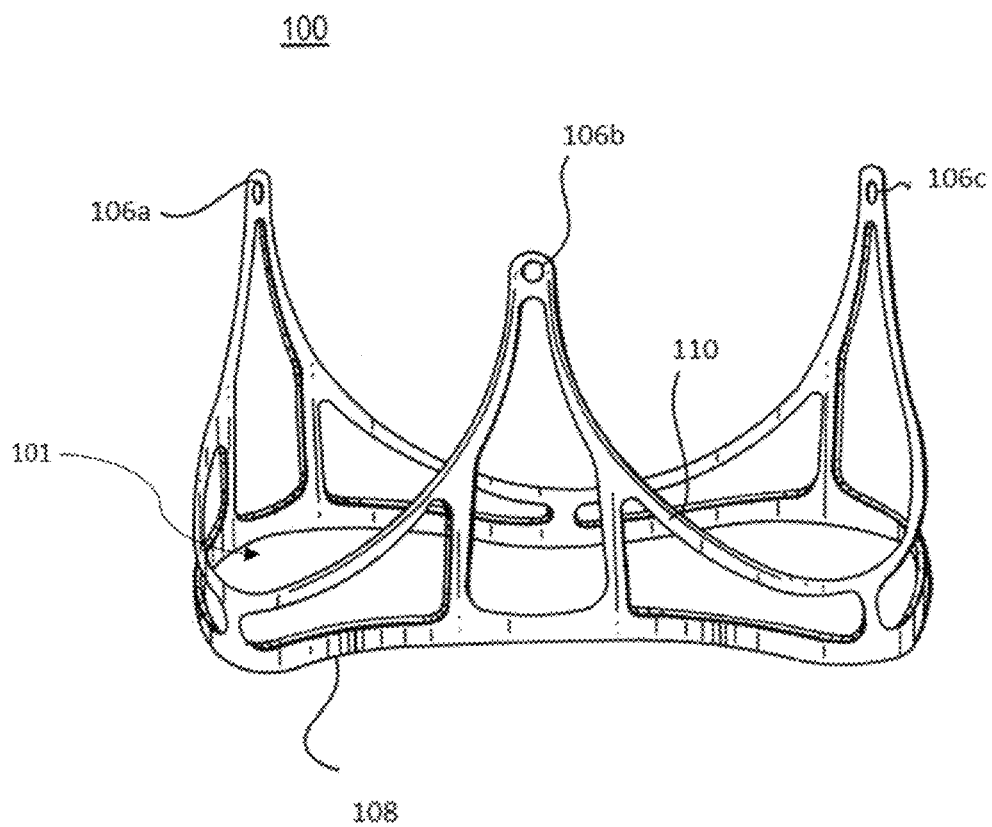
FIG. 1A is a perspective view of a frame of a surgical heart valve of the prior art.

FIG. 1A is a perspective view of a frame 100 for a prosthetic heart valve according to the prior art. Frame 100 is a component of a surgical heart valve, i.e., a prosthetic heart valve that is implanted in a patient through open chest, open heart surgery. Generally, certain embodiments of the present disclosure include frames similar to frame 100, although each embodiment includes a different feature that enables the frame to expand after implantation, in vivo, as will be described in further detail below. Expansion of the frame enables a sufficiently large transcatheter valve to be implanted within the surgical heart valve during a VIV procedure.

Referring to FIG. 1A, frame 100 is a hollow, non-collapsible annular stent-like structure. Frame 100 is referred to as "hollow" because the interior region 101 that is bounded by its annular structure is open. Frame 100 is typically made of biologically compatible metal, such as titanium (e.g., Ti 6Al-4V ELI Grade 23). A typical technique for making frame 100 is to cut it from a tube using a laser. Frame 100 is then typically electro-polished. Alternatively, frame 100 may be made from other biologically compatible materials, such as polymers, or a combination of metal and polymer.

Because the prosthetic heart valve being discussed is a tricuspid valve (e.g., for use in replacing a patient's aortic valve), frame 100 has three commissure posts 106a, 106b, and 106c that may be equally spaced from one another around the circumference of the frame. Each commissure post stands up from the annularly continuous base portion of the frame. The base portion includes a lower-most, blood-inflow edge portion 108. This blood-inflow edge portion may be scalloped as one proceeds around the frame to approximately match the natural scallop of the native valve annulus. In particular, this scallop may rise in the vicinity of each commissure post, and may fall between each annularly adjacent pair of commissure posts.

Frame 100 also includes an annularly continuous blood-outflow edge portion 110 (which merges with and becomes part of each commissure post 106). Outflow edge portion 110 may be much more deeply scalloped than the inflow edge portion. In particular, outflow edge portion 110 rises adjacent each commissure post 106 (actually merging into each commissure post), and falls between each annularly adjacent pair of commissure posts.

The inflow edge portion 108, outflow edge portion 110, and flexibility of frame 100 are designed to help ensure proper opening and coaptation of the finished valve in use. (Coaptation is the coming together of the outflow portions of the valve leaflets when the valve is closed.) Frame 100 is further designed to decrease maximum stresses in the frame in use, which gives the finished valve an increased safety factor.

Although titanium is mentioned above as a typical material from which frame 100 can be made, other materials are also possible. Some examples of other materials that may be suitable for use in making frame 100 include Elgiloy MP35N or polymers such as PEEK or acetal.

Figure 2:
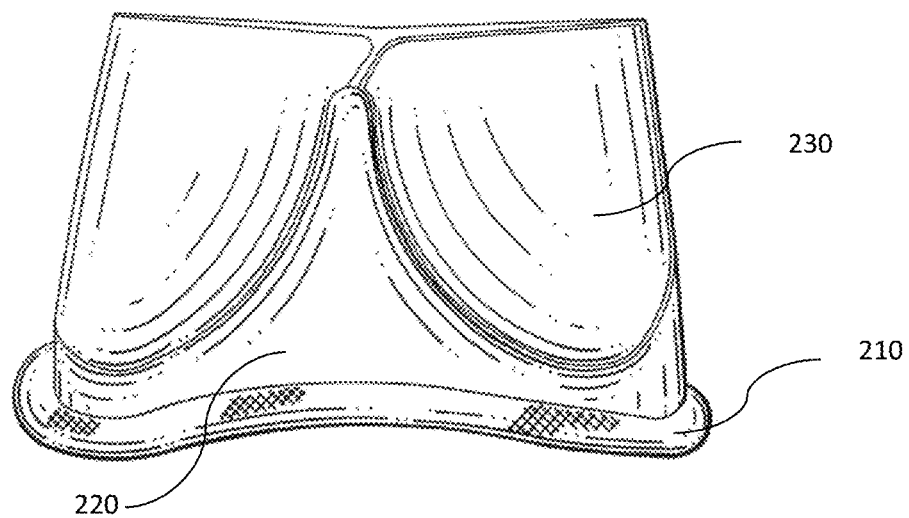
FIG. 2 is a perspective view of an embodiment of a surgical heart valve of the prior art.

FIG. 2 illustrates a prior art prosthetic heart valve 200 formed from frame 100. Prosthetic heart valve 200 may include a sewing cuff 210 and one or more layers of fabric and/or biological tissue covering the sewing cuff and frame 100. For example, a ring (not shown) formed of silicone or another appropriate material may be positioned around the outside of inflow edge portion 108 and may follow the scalloping of the inflow edge portion. A layer of fabric (not shown) may then be applied tightly over the inside surface of frame 100, over the outside surface of the frame, and around the exposed surfaces of the ring so that the fabric layer conforms to the outflow edge portion 110 of the frame. Sutures may be used to hold the fabric layer to the underlying structures.

Optionally, a fabric sleeve (not shown) may be sutured or otherwise attached to cover the top of each commissure post 106 prior to the application of the fabric layer. These fabric sleeves may help reduce the possibility that the tips of the commissure posts will poke through the fabric layer or any subsequently applied layers.

A layer of biological tissue 220 may then be applied over the fabric layer both inside and outside of frame 100 and may attach to the fabric-covered ring. The biological tissue may be mammalian pericardial tissue, such as bovine, porcine or equine pericardium, or other appropriate types of tissue. The tissue layer may be secured to the underlying structure by sutures. Additional tissue, preferably of the same type, may be cut to shape and assembled to the interior of the covered frame to form leaflets 230. The lower edges of the leaflets may follow the scalloped shape of inflow edge portion 108. All three leaflets shown in FIG. 2 may be formed from a single intact sheet of tissue. Rather than biological tissue, leaflets 230 and the outer covering of prosthetic heart valve 200 may be formed from a biocompatible polymer, or from a tissue/polymer combination. The various layers that may be applied to frame 100 to form surgical heart valve 200 are more fully described in U.S. Pat. No. 9,510,944, the disclosure of which is hereby incorporated by reference herein.

Figure 3:
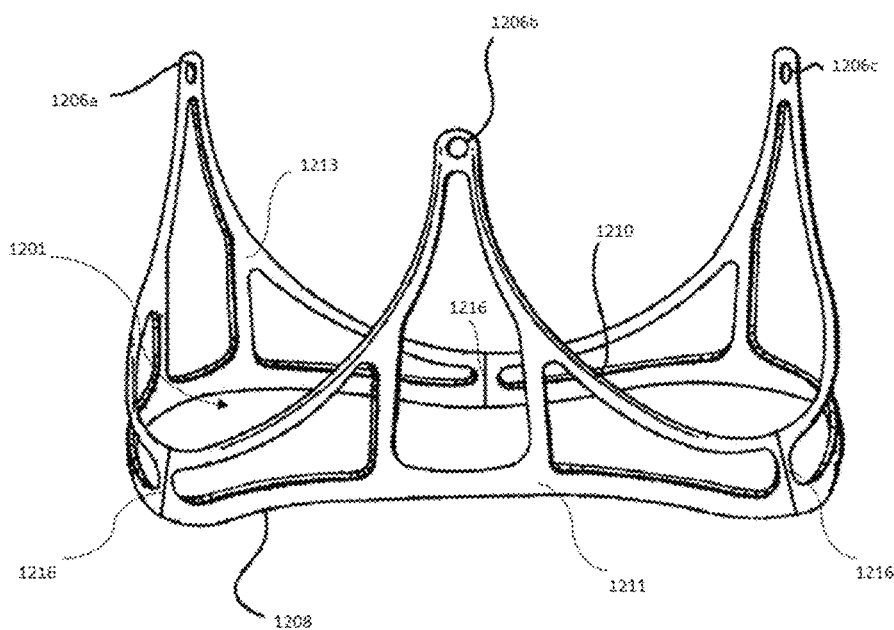
FIG. 3 is a perspective view of a frame of a prosthetic heart valve according to an embodiment of the present disclosure.

The prosthetic heart valves in accordance with the present disclosure may be similar to heart valve 200 described above, and may include the same fabric, tissue and/or polymer leaflets and covering layers, but may be modified to include features that allow the frame of the valve to expand after implantation, during a VIV procedure. Referring to FIG. 3, a frame 1200 that may be part of a surgical heart valve is similar in structure to frame 100, although frame 1200 includes expansion features that allow the frame to expand after implantation. One form of expansion feature may be the inclusion of at least one weakened portion in frame 1200. In the illustrated embodiment, the weakened portion is a groove 1216 scored into the frame. FIG. 3 shows three such grooves 1216 formed in frame 1200, although a lesser or greater number of grooves may be employed. Grooves 1216 may be incorporated in frame 1200 at the time of manufacture (for example, by laser cutting the grooves into the metal tube) or by adding the grooves to a previously fabricated frame (for example, by laser cutting, mechanically cutting, grinding or otherwise processing the tube to form the grooves therein).

Grooves 1216 extend along at least a portion of the width of the frame, measured from inflow edge 1208 to outflow edge 1210. At each of grooves 1216, the thickness of the frame between outer surface 1211 and inner surface 1213 is reduced such that the grooves are weaker than other portions of the frame. Grooves 1216 are designed to allow frame 1200 to preferentially break in a controlled manner, including at a known location and with the application of a predetermined stress. Grooves 1216 can have any length (measured between inflow edge 1208 and outflow edge 1210), depth (measured between outer surface 1211 and inner surface 1213), and width (measured along the circumference of the frame) that allows the frame to break in a desired manner.

In the illustrated embodiment, each groove 1216 extends along the entire width of frame 1200 from outflow edge 1210 to inflow edge 1208, although in other examples each groove may extend along only a portion of the width of the frame. Additionally, in the illustrated embodiment, the three grooves 1216 are equally spaced apart on the frame. Each groove 1216 is positioned between two of commissure posts 1206a, 1206b, and 1206c, preferably where the width of frame 1200 is narrowest. However, in other embodiments, the frame may include any number of grooves 1216 positioned at various locations on the frame which are not necessarily evenly spaced.

Frame 1200 may be part of a surgical heart valve, such as heart valve 200 described above. The surgical heart valve may be implanted in a patient whose native valve does not function properly. Although frame 1200 includes grooves 1216 or other weakened areas, these areas are sufficiently strong to remain intact and not break or deform during the implantation of the surgical heart valve. After a period of time, the surgical heart valve itself may cease to function as intended. This typically occurs in patients that are older and that can no longer tolerate the trauma of open chest, open heart surgery to replace the surgical heart valve. In such event, a collapsible transcatheter heart valve may be implanted using a less traumatic percutaneous procedure. In such procedure, the transcatheter heart valve is advanced to the target site in a collapsed condition, typically using a transfemoral or transapical approach, and deployed within the failing surgical valve.

In one embodiment, the transcatheter valve may be balloon expandable, and a deployment device may be used to deliver the valve and a dilation balloon to the target site. The transcatheter valve may be deployed within the failing valve, and the dilation balloon may be expanded within the transcatheter valve, exerting a radially outward force that expands the collapsed valve. As the dilation balloon applies the radially outward force to the transcatheter valve, the expanding valve transmits that force to the failing surgical valve. The exertion of that force on frame 1200 causes grooves 1216 to deform, e.g. stretch or break, such that the diameter of the frame symmetrically expands from a relatively small initial diameter to a relatively large expanded diameter, increasing the area of interior region 1201. Grooves 1216 can be sized and dimensioned such that they fail at a predetermined stress. As a result, a lower pressure balloon may be used to apply the appropriate force prior to over-expansion of the frame. This may help to prevent rupture of the tissue of the native annulus, which is more likely to occur if the frame is over-expanded. Once the transcatheter valve and frame 1200 have expanded, an evaluation can be made as to the adequacy of bloodflow therethrough.

In another embodiment, the transcatheter valve may be self-expanding and may expand upon deployment within the failing surgical valve. The expansion of the transcatheter valve applies a force on the surgical valve, causing it to also expand, allowing the transcatheter valve to expand to a sufficiently-sized diameter. In another embodiment, the surgical valve may be expanded by a dilating balloon before the self-expanding transcatheter valve is deployed within the surgical valve.

Figure 4:
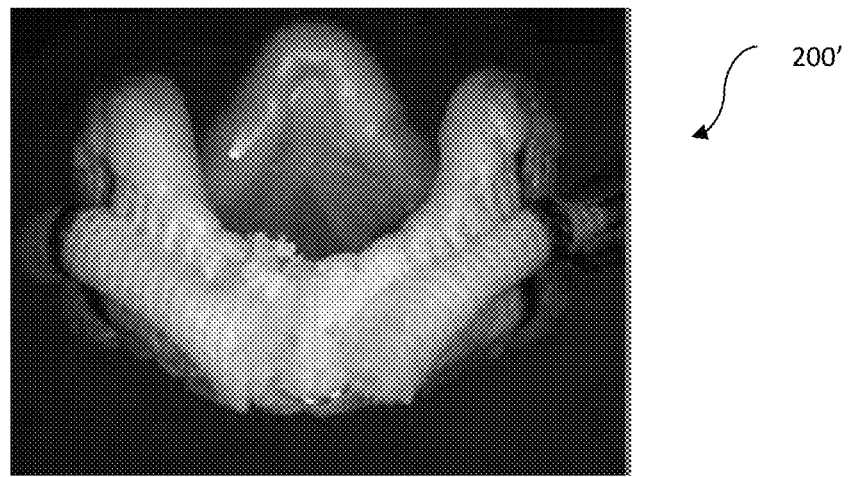
FIG. 4 is a perspective view of a valve having the frame of FIG. 1A with a fabric and/or tissue covering and a sewing cuff.

As discussed above, grooves 1216 may be added to frame 1200 after its manufacture but prior to its incorporation in prosthetic valve 200. Alternatively, frame 1200 may be manufactured to include grooves 1216. For example, FIG. 4 illustrates a prosthetic heart valve with a polymer frame (not shown) formed by molding, such as injection molding. The grooves may be molded into the frame by features in the molding die. Alternatively, the molding process itself may result in the formation of at least one knit line or groove. During the molding process, two or more flow fronts may be unable to bond or "knit" together perfectly, causing one or more localized weakened areas. The weakened areas result in preferential cracking of the frame when subjected to radial expansion forces. In another variant of this embodiment, the frame 1200 may be formed of metal with a layer of polymer molded over the frame at the desired locations for the grooves. The grooves may be scored into the polymer layer and may plastically deform or fracture when subjected to radial expansion forces, increasing the diameter of the frame. In some embodiments, depending on the polymers used, the frame may radially expand by virtue of the expansion of the polymer, without the corporation of grooves in the frame.

Figure 5:
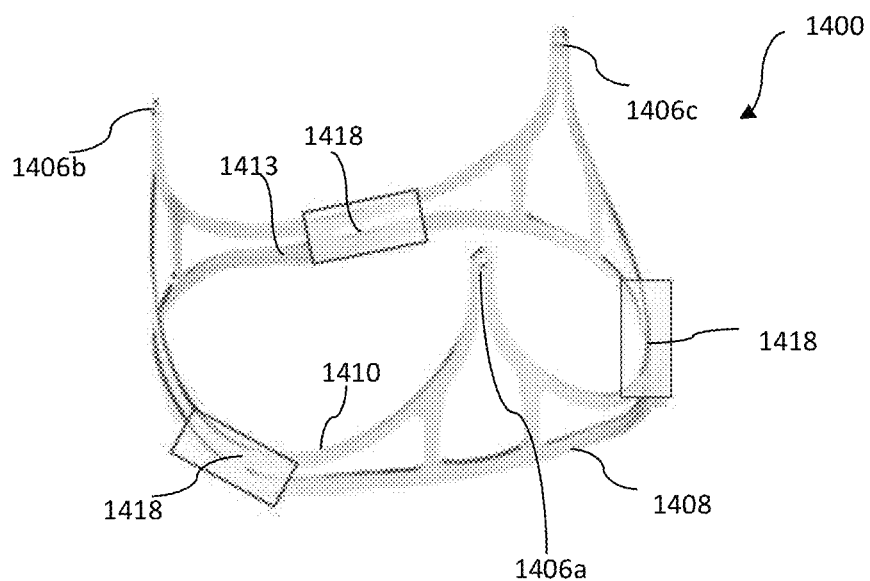
FIG. 5 is a perspective view of a frame of a prosthetic heart valve according to another embodiment of the present disclosure.

FIGS. 5-6 show an expandable stent frame 1400 according to an alternate embodiment of the present disclosure. Frame 1400 may be part of a surgical heart valve, such as heart valve 200 described above. The overall structure of frame 1400 is similar to that of frame 100 and need not be described herein. Frame 1400 differs from frame 100 in that it includes at least one expansion zone 1418 having a feature that allows for expansion of the frame after implantation into a patient's body.

As shown in FIG. 5, frame 1400 includes three expansion zones 1418 annularly spaced on the frame, although the frame may include a lesser or greater number of such expansion zones. Expansion zones 1418 may be equally spaced from one another around the circumference of frame 1400. Expansion zones 1418 may be integrated into the base portion of frame 1400 and may extend along the width of the frame from inflow edge 1408 to outflow edge 1410. In the illustrated embodiment, each expansion zone 1418 is positioned between two of commissure posts 1406a, 1406b, and 1406c such that the expansion zone is between two generally rigid portions of the frame. Accordingly, each expansion zone 1418 is positioned on a generally narrow portion of the frame. In alternative embodiments, however, any number of expansion zones may be positioned anywhere on frame 1400. Expansion zones 1418 may be formed of elements or materials that undergo plastic deformation when subjected to a predetermined force or expanded beyond a predetermined dimension, which prevents elastic rebound of the zones after expansion. These elements may include bendable structures, springs, or coils that are welded or crimped to the frame and undergo plastic deformation upon expansion. In other embodiments, the expansion zones, as described above, may include a layer of polymer molded over the expansion zones. The polymer regions yield upon application of a known amount of force, while the surrounding rigid metal areas are capable of withstanding this amount of force.

Figure 6A:
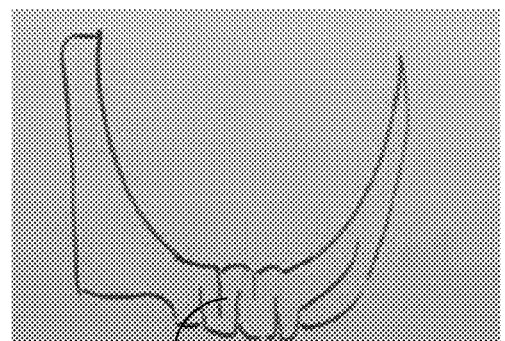
FIGS. 6A and 6B are enlarged partial views of the frame of FIG. 5 in an initial configuration and an expanded configuration, respectively.
Figure 6B:
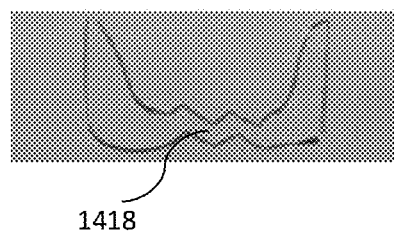

In FIGS. 6A and 6B, expansion zones 1418 include expandable zig-zag segments integrated into frame 1400 during manufacture by cutting the segments from the tube using a laser. As shown by comparison of FIGS. 6A and 6B, each expansion zone 1418 increases in length from an initial length (FIG. 6A) to an expanded length (FIG. 6B) after a predetermined radially outward force is applied to frame 1400 from the interior thereof. As a result of the elongation of expansion zones 1418, frame 1400 may diametrically expand from a relatively small initial diameter to a relatively large expanded diameter.

Figure 7:
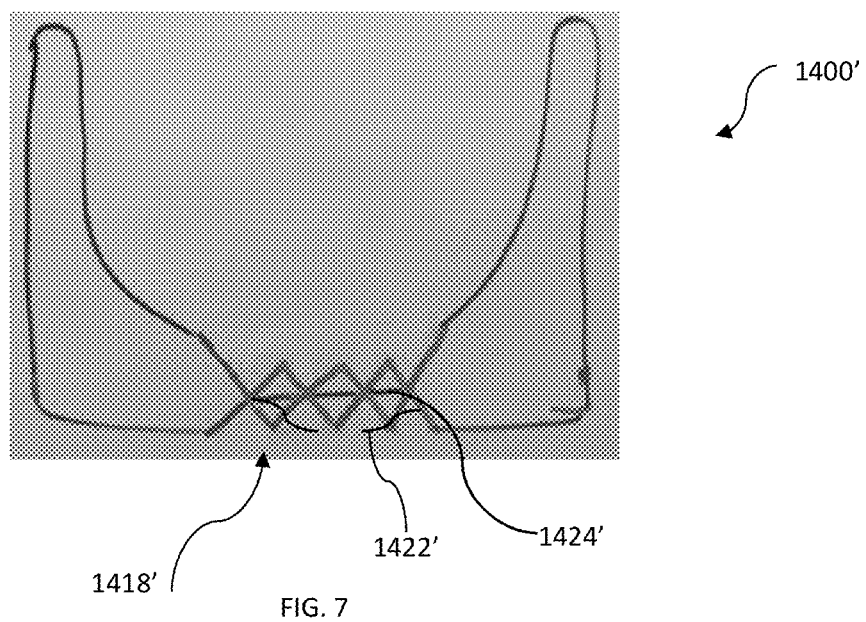
FIG. 7 is a highly schematic partial view of a frame of a prosthetic heart valve according to yet another embodiment of the present disclosure.

FIG. 7 shows frame 1400', which is substantially similar to frame 1400, except that frame 1400' includes expansion zones 1418' having expandable segments arranged in a diamond pattern. Additionally, expansion zones 1418' include frangible members 1422' integrated between separate segments of frame 1400'. In the illustrated embodiment, frangible member 1422' includes one or more lengths of suture or another filament that extends across the expansion zone 1418' between two substantially rigid portions of the frame. Frangible members 1422' are designed to prevent the expansion zones from expanding until a predetermined radially outward force is exerted on the frame. As such, frangible members 1422' prevent the unintended expansion of expansion zones 1418', and thus frame 1400', which may otherwise occur during surgical implantation.

As radially outward forces are applied to frame 1400', even unintended forces that may occur during implantation of the valve, tension is created in the frangible members 1422'. However, the frangible members 1422' are designed to remain intact until a threshold force is applied. This threshold force is greater than the unintended forces that could occur during implantation of the frame. However, when the threshold force is reached or exceeded, such as by expansion of a dilation balloon, frangible members 1422' rupture, enabling expansion zones 1418' to expand and the segments of frame 1400' to separate from one another. Rather than using frangible member 1422' that rupture, the expandable segments of expansion zones 1418' themselves may be configured to expand only when the threshold force has been applied. As such, the segments will not expand from implantation forces, but only when it is desired for them to do so.

In a preferred embodiment, frame 1400' may also include a second or limiting filament 1424' that may be structured similarly to frangible member 1422'. Limiting filament 1424' may be designed to withstand forces greater than the threshold force, and therefore may prevent the expansion of frame 1400' beyond a certain maximum dimension. As a result, even if the dilation balloon is over-expanded, the frame is prevented from expanding further than a maximum desired diameter by limiting filament 1424', which would constrain the frame to the desired expanded size despite the force being applied to the balloon. A frame may include frangible member 1422', limiting filament 1424', or both of these devices.

It will be appreciated that frames 1200 and 1400 described above may also include frangible members 1422' and/or limiting filaments 1424'. For example, frame 1200 may include limiting filaments 1424' to constrain expansion of the frame beyond a maximum upon the deformation (stretching or rupturing) of grooves 1216. Frame 1400, on the other hand, may include both frangible members 1422' and limiting filaments 1424' to prevent the unintended expansion of expansion zones 1418', such as during valve implantation, as well as the expansion of frame 1400 beyond a maximum dimension. It will also be appreciated that frangible members 1422' and limiting filaments 1424' need not be in the form of filaments, but may be any structures capable of providing the functions described above. Moreover, frangible members 1422' and limiting filaments 1424' need not be separate elements, but rather may be a single element capable of performing both of the described functions. For example, a coiled spring could be sufficiently stiff to resist expansion by radial forces less than the threshold force, but once the threshold force is exceeded, be capable of expanding only to a maximum length. It will thus be apparent that frangible member 1422' need not be frangible, and that limiting filament 1424' need not be filament.

Regardless of which structures form the expansion zones, as discussed above, each of the expansion zones may be sized and shaped to be substantially identical to one another such that each zone expands by about the same amount with the applied radially outward force. Upon the expansion of the expansion zones, the diameter of the frame becomes greater. The radially outward force can be exerted on the frame by a balloon or other expansion mechanism positioned inside the frame either prior to or during a VIV procedure, as described above in connection with frame 1200.

Figure 8:
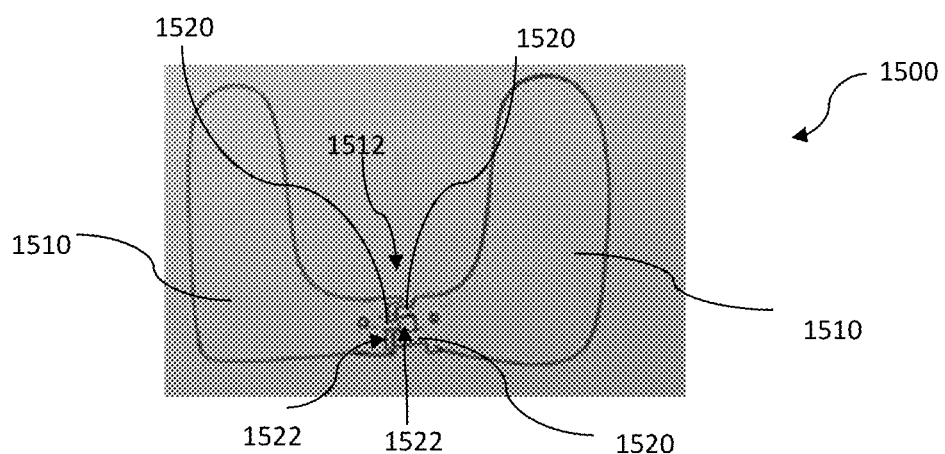
FIG. 8 is a highly schematic partial view of a frame of a prosthetic heart valve according to still another embodiment of the present disclosure.

FIG. 8 shows expandable frame 1500 according to another embodiment of the present disclosure. The overall structure of frame 1500 may be similar to those of frames 100, and 1400 and 1400', and is not repeated here. Frame 1500 includes a plurality of interlocking segments 1510 that collectively form the frame. Each of segments 1510 generally has the shape of a portion of an annulus, such that segments 1510 may collectively form a complete annular structure. For example, for frames 1500 having two segments 1510, each of the segments may generally have the shape of a semi-circle. Alternatively, each of segments 1510 may be arc shaped, with a first segment defining an arc of greater than 180 degrees and the other segment defining an arc of less than 180 degrees. For frames 1500 having more than two segments 1510, each of the segments may define an arc of less than 180 degrees.

Segments 1510 are connected to one another by at least one locking member 1512 that prevents unintended circumferential and/or radial displacement of the segments during implantation of the surgical valve. In certain embodiments, a plurality of locking members 1512 may connect segments 1510 to one another. Locking member 1512 may be any locking feature known in the art. In the illustrated embodiment, locking members 1512 consist of a plurality of projections 1520 extending from one of segments 1510 and a plurality of complementary recesses 1522 formed in the other one of the segments to form a Lego®-type fit between the segments. In an alternate arrangement, one of segments 1510 may include an alternating arrangement of both projections 1520 and recesses 1522 that mate with complementary projections and recesses on the other segment.

Projections 1520 and recesses 1522 may be joined to one another in an initial locked configuration of frame 1500 in which the frame has an initial diameter. Frame 1500 may include a mechanism that holds segments 1510 in this locked configuration. One such mechanism may be the friction fit between projections 1520 and recesses 1522. Another such mechanism may be a weak adhesive or weak welds joining segments 1510 to one another. Yet another such mechanism may be sutures, filament or tape joining segments 1510 together. A still further such mechanism may be a mechanical snap fit joining projections 1520 to recesses 1522, or otherwise joining segments 1510 to one another. Additional forms of locking mechanisms that may be employed will be apparent to those of ordinary skill in the art. The locking mechanism may be applied at each of the locations at which one segment 1510 interfaces with an adjacent segment, or at fewer than all of these locations. In each case, the locking mechanism holding segments 1510 together is such that, upon the application of a radially outward force to frame 1500 that meets or exceeds a predetermined threshold, the mechanism will release, enabling the segments to move away from one another and the diameter of the frame to increase.

Although frame 1500 is described above as including two segments 1510, the frame may include more than two segments. Segments 1510 may be identical to one another or they may be shaped differently from one another. For example, a first segment 1510 may include one commissure post, and a second segment 1510 may include two commissure posts. In an alternative arrangement, frame 1500 may include three identical segments 1510, each having one commissure post (for the frame of a valve having three leaflets).

As with the other embodiments described above, frame 1500 may include a feature to prevent its over expansion. In one example, one or more recesses 1522 may include a ratchet mechanism (not shown) that allows projection 1520 to be inserted in a first direction into the recess, but prevents the projection from moving past a certain point in the opposite direction out from the recess. The ratchet mechanism may include a tooth in recess 1522 and at least one complementary tooth on projection 1520. The teeth are sized and shaped to allow them to move past one another as projection 1520 is moved in the first direction into recess 1522, but to prevent them from moving past one another in the opposite direction. Thus, the teeth are engaged with one another when frame 1500 has expanded to a predetermined maximum diameter, thereby preventing the frame from expanding beyond that diameter.

Figure 1B:
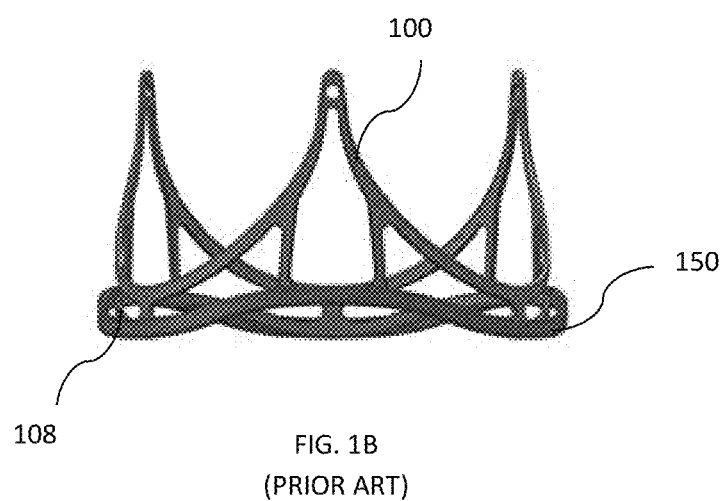
FIG. 1B is a perspective view of a frame having a support ring around the outer surface of the frame of the prior art.

In a variant of the present disclosure, any of the heart valves described above may include a ring positioned around the outside of the frame forming the heart valve. One example of such a ring is ring 150 positioned around frame 100 in FIG. 1B. Ring 150 is disposed near the inflow edge 108 of the frame. In the illustrated embodiment, ring 150 is formed to track the scalloped shape of the inflow edge 108. Ring 150 provides structural support to frame 100 and helps to prevent ovalization of the frame. Additionally, ring 150 may be highly radiopaque, which may help to enhance identification of the inflow edge of the heart valve under fluoroscopy to facilitate the proper positioning of the valve.

The rings of the present disclosure are designed to be expandable and may be positioned around any of the frames 100, 1200, 1400, and 1500, described above. The rings may incorporate the same or different expansion features as the frame the ring is disposed on. Thus, one expansion technique of the present disclosure may be employed to expand the frame after implantation while a different expansion technique of the present disclosure may be utilized to expand the ring after implantation.

Figure 9:
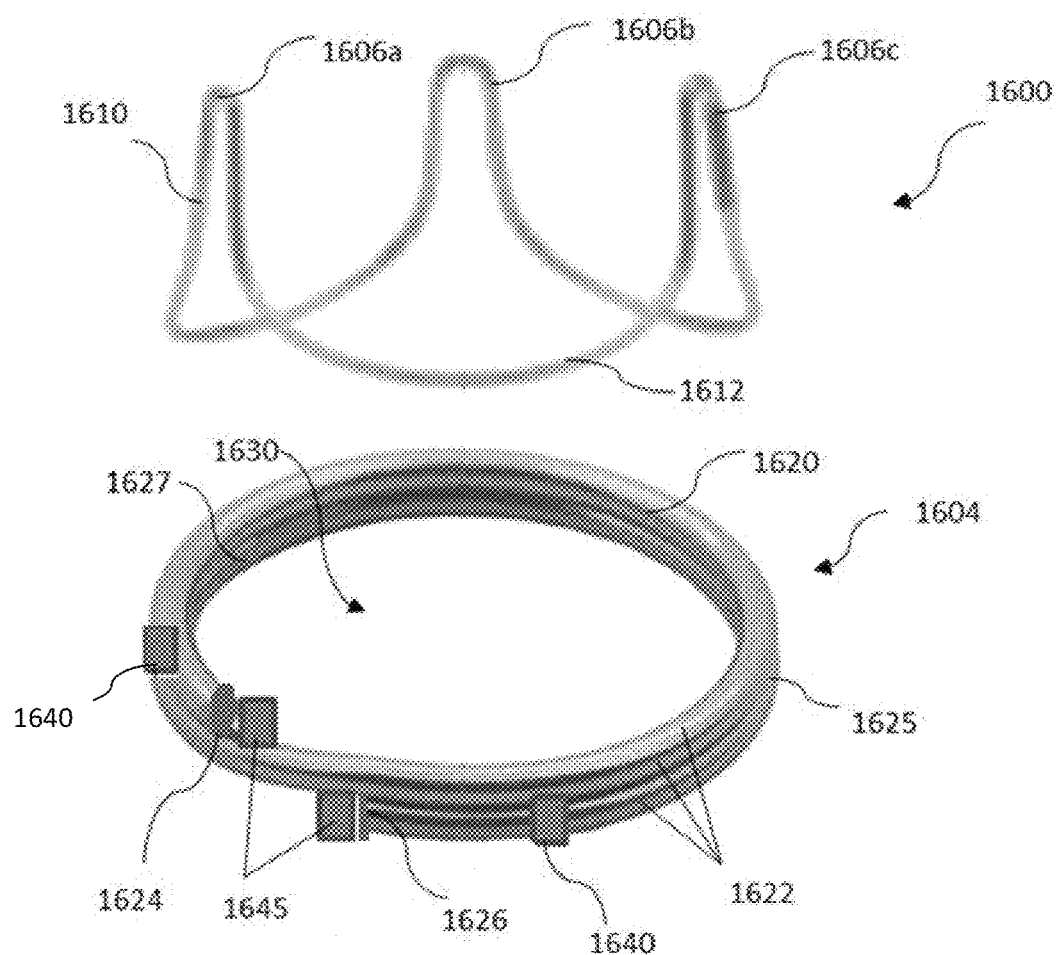
FIG. 9 is an exploded perspective view of a frame system for a prosthetic heart valve according to an embodiment of the present disclosure.

An expandable frame 1600 according to another embodiment of the present disclosure is shown in FIG. 9. Frame 1600 utilizes a two-piece design including an expandable base 1604 and a leaflet frame 1610 coupled to one another. Leaflet frame 1610 is annularly shaped and includes commissure posts 1606a, 1606b, and 1606c extending up from support 1612. Leaflet frame 1610 supports a plurality of leaflets, and base 1604 supports a sewing cuff such that frame 1600 may form a valve similar to valve 200. Leaflet frame 1610 may be coupled to base 1604 in a manner that allows the base and the leaflet frame to expand. For example, suture may be wrapped around an upper turn 1622 of base 1604 and commissure posts 1606 of leaflet frame 1610 to couple the frame to the base. Due to the flexible nature of the suture, neither the base nor the leaflet frame is prevented from expanding. Alternatively, the base may have suture receiving holes within one or more turns 1622. Frame 1600 forms part of a non-collapsible surgical heart valve that may have the same fabric, tissue and/or polymer leaflets and covering layers as heart valve 200 described above. Frame 1600 is configured to expand during a VIV procedure, and may be expanded in a similar manner to frame 1200 as described above.

Base 1604 is annularly shaped and includes a helically wound coil 1620 formed from a material that plastically deforms when expanded to a larger diameter. Such materials may include biocompatible ductile metals, or other biocompatible metals, such as spring steel, that exhibit elastic properties under low stresses, but that deform plastically beyond a threshold stress. Coil 1620 includes a plurality of turns 1622 that terminate in free ends 1624 and 1626, and that collectively define an outer surface 1625 of the coil, an inner surface 1627 of the coil opposite the outer surface, and a hollow interior 1630. The material forming each of turns 1622 has a diameter that is less than the diameter of free ends 1624 and 1626. In other words, the free ends of the coil have an enlarged diameter in comparison. When an outward radial force is exerted on the inside of coil 1620, i.e., against inner surface 1627, during a VIV procedure, free ends 1624 and 1626 move away from one another as the turns 1622 of the coil slide with respect to each other. In this manner, coil 1620 plastically expands from a first condition having a first diameter to a second condition having a relatively larger diameter. The outward radial force can be applied to inner surface 1627 by a balloon, an implanted transcatheter valve, or other known methods.

Coil 1620 includes a pair of expansion stops 1640 that limit the amount that the coil is capable of expanding. Expansion stops 1640 may be obstruction elements that prohibit turns 1622 from expanding beyond a desired maximum diameter. One of expansion stops 1640 is affixed (by welding or otherwise) to the turn 1622 adjacent the outer turn having free end 1624 and includes an aperture sized so that the outer turn can slide therethrough during expansion of coil 1620. The other expansion stop is affixed (by welding or otherwise) to the turn 1622 adjacent the outer turn having free end 1626 and includes an aperture sized so that the outer turn can slide therethrough during expansion of the coil. Thus, in FIG. 9, the turn 1622 below free end 1624 includes an expansion stop 1640, and the turn above free end 1626 also includes an expansion stop 1640. The aperture in each of expansion stops 1640 has a diameter that is less than the diameter of free ends 1624 and 1626. As a result, turns 1622 are able to readily slide through expansion stops 1640 during expansion of coil 1620 until free ends 1624 and 1626 reach the expansion stops. Since the diameter of free ends 624 and 626 is greater than the diameter of the apertures in expansion stops 1640, the free ends are unable to slide through the expansion stops, obstructing further expansion of coil 1620.

During the initial implantation of the surgical heart valve, coil 1620 may experience radial forces exerted on the outside of the ring, i.e., against outer surface 1625. These radial forces may cause turns 1622 to move with respect to each other in an opposite direction to contract coil 1620. Coil 1620 may include a pair of reduction stops 1645 that prevent or limit the contracting of the coil.

One of reduction stops 1645 is affixed (by welding or otherwise) to the turn adjacent the outer turn having free end 1624, and is positioned in close proximity to that free end. The other reduction stop 1645 is affixed (by welding or otherwise) to the turn adjacent the outer turn having free end 1626, and is positioned in close proximity to that free end. Reduction stops 1645 are solid (i.e., they do not include apertures as do expansion stops 1640) and are positioned in the movement paths of free ends 1624 and 1626, respectively. As turns 1622 move with respect to each other in a contraction direction, each of free ends 1624, 1626 will contact an adjacent reduction stop 1645. This engagement of free ends 1624, 1626 with reduction stops 1645 blocks turns 1622 from sliding relative to one another in a contraction direction, preventing a reduction in the diameter of coil 1620.

According to a first aspect of the disclosure, a prosthetic heart valve includes a non-collapsible annular frame having annularly spaced commissure posts and an annulus portion disposed adjacent an inflow edge, the frame being configured to expand from an initial condition having a first diameter to an expanded condition having a second diameter larger than the first diameter when a predetermined force is applied to an inner surface of the frame; and a valve assembly connected to the frame and including a plurality of leaflets; and/or the frame may have an outflow edge opposite the inflow edge, a distance between the outflow edge and the inflow edge defining a width of the frame, and a weakened portion may extend along at least a portion of the width of the frame, the weakened portion being configured to deform when the predetermined force is applied to the inner surface of the frame; and/or the weakened portion may be a groove in the frame that extends from the outflow edge to the inflow edge; and/or a plurality of weakened portions may extend along a width of the frame and may be annularly spaced on the frame; and/or each of the plurality of weakened portions may be configured to deform at substantially the same predetermined force so that the frame expands symmetrically; and/or the frame may include a plurality of segments that are engaged with one another when the frame is in the initial condition and that are separated from one another when the frame is in the expanded condition; and/or the frame may include a limiting member connecting a first one of the segments to a second one of the segments, the limiting member enabling the frame to expand from the first diameter to the second diameter, but preventing the frame from expanding to a diameter larger than the second diameter; and/or the prosthetic heart valve may include a locking member configured to interlock the segments when the frame is in the initial condition; and/or the locking member may include a projection on a first one of the segments and a corresponding recess on a second one of the segments, the projection being configured to matingly fit within the recess to interlock the segments in the initial position; and/or the projection may include a first tooth oriented in a first direction and the recess may include a second tooth oriented in a second direction opposite the first direction, the teeth being sized and shaped so that the first tooth is able to move past the second tooth to a locked position as the projection is moved in a first movement direction into the recess, but so that the first tooth is unable to move past the second tooth as the projection is moved in a second movement direction, whereby with the first and second teeth in the locked position, the first one of the segments is unable to move in the second movement direction away from the second one of the segments; and/or the frame may include an expansion zone having a first length in the initial condition of the frame and a second length larger than the first length in the expanded condition of the frame; and/or the frame may include a plurality expansion zones annularly spaced about the frame; and/or the expansion zone may plastically deform to the second length; and/or the expansion zone may be formed of a spring or a coil.

According to another aspect of the disclosure, a prosthetic heart valve includes an annular base formed of a coil having a plurality of turns, the base being configured to expand from an initial condition having a first diameter to an expanded condition having a second diameter larger than the first diameter when a predetermined force is applied to an inner surface of the base; a leaflet frame having a plurality of annularly spaced commissure posts; and a valve assembly connected to the frame at the commissure posts, the valve assembly including a plurality of leaflets; and/or the turns may slide with respect to one another to move the base from the initial condition to the expanded condition; and/or the base may include two expansion stops, each expansion stop being fixedly connected to a respective one of the turns, the expansion stops being configured to prevent the base from expanding to a diameter larger than the second diameter; and/or the plurality of turns may have a first free end and a second free end, the first free end and the second free end each having a first diameter, greater than a second diameter of a remainder of the turns, each of the expansion stops having an aperture with a diameter greater than the second diameter and less than the first diameter, whereby the remainder of the turns are able to pass through the apertures during expansion of the base and the free ends of the turns are unable to pass through the apertures during expansion of the base; and/or the base may include two contraction stops, each contraction stop being fixedly connected to a respective one of the turns and being configured to prevent the base from contracting to a diameter less than the first diameter.

According to another aspect of the disclosure, a method of implanting a transcatheter heart valve within a surgical heart valve previously implanted in a patient includes expanding a diameter of the implanted surgical heart valve from a first diameter to a second diameter larger than the first diameter, and deploying a transcatheter heart valve within the implanted surgical heart valve; and/or the expanding step may include positioning a dilation balloon within the implanted surgical heart valve and expanding the balloon; and/or the transcatheter heart valve may be self-expanding, and the expanding and deploying steps may occur simultaneously from the expansion of the transcatheter heart valve; and/or the surgical heart valve may include an annular coil having a plurality of turns, and the expanding step may include sliding the turns of the surgical heart valve with respect to one another; and/or the second diameter of the surgical heart valve may be a predetermined maximum diameter.

According to another aspect of the disclosure, a system for repairing a damaged native heart valve includes a surgical heart valve having a non-collapsible annular frame with annularly spaced commissure posts and an annulus portion disposed adjacent an inflow edge, and a valve assembly connected to the frame and including a plurality of leaflets, the frame being configured to expand from an initial condition having a first diameter to an expanded condition having a second diameter larger than the first diameter when a predetermined force is applied to an inner surface of the frame; and a transcatheter heart valve deployable within the surgical heart valve and configured to properly function when the frame of the surgical heart valve is in the expanded condition; and/or the frame of the surgical heart valve may have an outflow edge opposite the inflow edge, a distance between the outflow edge and the inflow edge defining a width of the frame, and a weakened portion may extend along at least a portion of the width of the frame, the weakened portion being configured to deform when the predetermined force is applied to the inner surface of the frame.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
a non-collapsible annular frame having annularly spaced commissure posts and an annulus portion disposed adjacent an inflow edge, the frame being configured to expand from an initial condition having a first diameter to an expanded condition having a second diameter larger than the first diameter when a predetermined force is applied to an inner surface of the frame; and
a valve assembly connected to the frame and including a plurality of leaflets,
wherein the frame has an outflow edge opposite the inflow edge, a distance between the outflow edge and the inflow edge defining a width of the frame, and a deformable portion extends along at least a portion of the width of the frame, the deformable portion being configured to deform when the predetermined force is applied to the inner surface of the frame,
wherein a plurality of deformable portions extend along the width of the frame and are annularly spaced on the frame,
wherein each of the plurality of deformable portions is coupled to a pair of two adjacent portions of the frame,
wherein each of the pairs of two adjacent portions of the frame is coupled by a frangible member designed to prevent the deformable portions from deforming until the predetermined force is applied to the inner surface of the frame,
wherein the frangible member is a suture or filament,
wherein each of the plurality of deformable portions includes an expansion zone formed of a spring or a coil having a first length in the initial condition of the frame and a second length larger than the first length in the expanded condition of the frame.

2. The prosthetic heart valve of claim 1, wherein each of the plurality of deformable portions is configured to deform at substantially the same predetermined force so that the frame expands symmetrically.

3. The prosthetic heart valve of claim 1, wherein the expansion zone plastically deforms to the second length.

4. A prosthetic heart valve, comprising:
an annular base formed of a coil having a plurality of turns, the base being configured to expand from an initial condition having a first diameter to an expanded condition having a second diameter larger than the first diameter when a predetermined force is applied to an inner surface of the base;
a leaflet frame having a plurality of annularly spaced commissure posts;
a valve assembly connected to the frame at the commissure posts, the valve assembly including a plurality of leaflets,
wherein the base includes two expansion stops, each expansion stop being fixedly connected to a respective one of the turns, the expansion stops being configured to prevent the base from expanding to a diameter larger than the second diameter.

5. The prosthetic heart valve of claim 4, wherein the turns slide with respect to one another to move the base from the initial condition to the expanded condition.

6. The prosthetic heart valve of claim 4, wherein the plurality of turns have a first free end and a second free end, the first free end and the second free end each having a first diameter greater than a second diameter of a remainder of the turns, each of the expansion stops having an aperture with a diameter greater than the second diameter and less than the first diameter, whereby the remainder of the turns are able to pass through the apertures during expansion of the base and the free ends of the turns are unable to pass through the apertures during expansion of the base.

7. The prosthetic heart valve of claim 4, wherein the base includes two contraction stops, each contraction stop being fixedly connected to a respective one of the turns and being configured to prevent the base from contracting to a diameter less than the first diameter.

* * * * *